United States Patent [19]
Parodi

[11] Patent Number: 5,911,733
[45] Date of Patent: *Jun. 15, 1999

[54] ENDOVASCULAR EXPANDER OF A NON-MIGRANT POSITIONING

[76] Inventor: Juan Carlos Parodi, Blanco Encalada 1543/47, 1 piso, Capital Federal, Buenos Aires, Argentina

[*] Notice: This patent issued on a continued prosecution application filed under 37 CFR 1.53(d), and is subject to the twenty year patent term provisions of 35 U.S.C. 154(a)(2).

[21] Appl. No.: 08/810,807

[22] Filed: Mar. 6, 1997

[30] Foreign Application Priority Data

Mar. 6, 1996 [AR] Argentina .................................. 335651

[51] Int. Cl.$^6$ ................................................. A61M 29/00
[52] U.S. Cl. .............................. 606/198; 606/200; 623/1; 623/12
[58] Field of Search ..................... 606/198, 191, 606/195, 200; 623/1, 12

[56] References Cited

U.S. PATENT DOCUMENTS

| | | | |
|---|---|---|---|
| 5,108,418 | 4/1992 | Lefebvre | 606/200 |
| 5,234,458 | 8/1993 | Metais | 606/191 |
| 5,562,726 | 10/1996 | Chuter | 606/195 X |
| 5,593,417 | 1/1997 | Rhodes | 606/198 X |
| 5,630,829 | 5/1997 | Lauterjung | 606/198 |
| 5,681,345 | 10/1997 | Euteneuer | 606/198 |
| 5,681,346 | 10/1997 | Orth et al. | 606/198 |

*Primary Examiner*—Michael H. Thaler
*Attorney, Agent, or Firm*—Levisohn, Lerner, Berger & Langsam

[57] ABSTRACT

ENDOVASCULAR EXPANDER, OF NON MIGRANT POSITIONING; including a tubular body—generally structured by a wire mesh—which, tensed in the sense of its diametrical expansion against the internal surfaces of the vessel of application, is able to be introduced in it in order to maintain or increase the lumen of said vessel; wherein, outwardly, the expander has a plurality of unidirectional anchorages in proximal arrangement to said tubular body and in the sense of its generatrix; each one of said anchorages possesses two opposite ends of—union to the body of the expander and of vascular anchorage, respectively—of which: that one of union is articulable with respect to said body, while that one of vascular anchorage, as of said link is projected freely in proximal arrangement to the body of said expander; so that, being said endovascular expander applied—the anchorage ends being oriented in equal direction to that of the flow of the bloodstream—said anchorages are capable of opening in contraposition to the migrant effect of the expander.

8 Claims, 2 Drawing Sheets

ND OVASCULAR EXPANDER OF A NON-
MIGRANT POSITIONING

I BACKGROUND OF THE INVENTION

The present invention consists of an endovascular expander, of a non migrant positioning, and its purpose is to offer a means for positional self-fastening of said expander, preventing its dragging by the bloodstream.

Lately, in the field of medicine, endovascular treatments have had particular diffusion. These are characterized by being carried out through the interior of the lumen of the vessels, instead of entering through surgery, that is to say, making an incision in the tissues until reaching the artery or affected vein.

Such endovascular treatments are carried out in the lumen of the vessel, with various purposes and the employment of different means, either:

to produce the expansion of the artery or of the vein,
dissolve thrombus in its interior,
close abnormal communications of these vessels, among them or to the neighboring tissues,
to cover the surface of the same with a prosthesis, as a means of "wrapping",
return a dilated artery (aneurysm) to its normal caliber,
isolate the internal surface of an artery from the physical or chemical elements of the blood, after accomplishing an expansion with a balloon ("internal bypass"); etc.

After American radiologist Charles Dotter researches, and within the endovascular techniques, the endovascular placement expanders has constituted an important advance, especially the elastic and permeable tubular structures that are normally known by their English denomination: "stents". So that, from here onwards and throughout this report they will be mentioned indistinctively as endovascular "expanders" or, simply, "stents".

The "stents"—generally structured in special metallic meshes—form very thin expansible pipes, generators of radial forces capable of maintaining the vessels open and in contraposition to the tensions that tend to close them.

In essence, it can be said that there exist three types of "vascular" stents: the thermosensitive ones, that adopt predetermined shapes at different temperatures, in particular that of the human body (as can be seen, for example, in the line Nitinol; in U.S. Pat. No. 4,425,908, etc.); the ones expansible with a balloon (as it is explained in European Patent EP 378.151); and the ones self-expansible through elasticity (as spread in U.S. Pat. No. 4,580,568).

The ""vascular" stents are being used for the treatment of angioplasties that turned out to be sub-optimum; to treat dissections after angioplasties and, lately, to assure endoluminal grafts, as well as acting as prosthesis for various applications, (Perrone, R and others, "Endoluminal prosthesis", Rev. Arg. de Cirugía", 1992; 62:146–149; Mazzariello, R.: "Applicacion percutánea de protesis biliares expandibles", in Revista Argentina de Cirugía, 1990: 979–983; etc.).

Also expanders and combined grafts have been used in numerous applications, such as: aneurysms, dissections, vascular trauma and arterial occlusion diseases.

Now then; one of the principal complications that result from the employment of the "Stent-graft" (expander graft) is the migration of the device, dragged by the own bloodstream. This occurs, for example, with the very thin "zigzag" wire pipes as the ones developed by Gianturco in 1985 and in the wire prosthesis of Mazzariello, (Rev. Arg. de Cirugía, 1990: 979–983), which by virtue of its particular structure scarcely frictioning, it is capable of being slid easily to a place not wished; being possible that this migration is tardily detected, even after its correct positioning.

To offset such problem, the fixing means of many expanders or "stents" is friction.

Also, and with the same anti-migrant purpose, many devices of the indicated type possess hooks or tabs added as a mechanism for the collaboration of subjection. J. F. Dumond, for example, developed a model to which it added external spicules of the same material of the prosthesis. (Dumond, J. F. "A dedicated tracheobrochial stent". Chest, 1990; 97-328-322), that had a limited diffusion, probably due to the problems observed upon intending to solve the sliding by means of rigid projections intended to be nailed in the walls of the vessel.

In effect; the drawback of using hooks, thorns or tabs is that many times the place of positioning of the arterial wall is found calcified and, therefore, it can not be penetrated. Thus, when the hook, the thorn or the tab is outside of the arterial wall— due to impossibility of penetrating it—a space is created between said wall and the expander, making possible the flow of blood out of the graft and thus, originating a peri-prosthesic loss.

In order to solve the outlined drawbacks, the inventor has developed an extra mechanism of subjection different from the hooks, tabs or rigid spicules, being stemmed from the observation of the scales that cover the body of the fish. In effect; when the hand is passed very gently throughout the surface of a fish, as long as the direction of the movement is in the direction sense of the scales, no resistance shall be found; but when the hand is moved in the opposite direction, resistance will be found.

Similarly, the new non-skid means—that collaborates to maintain the "stent" positioned in the correct place—does not act, unless it is and results necessary; in such case multiple plates that will be opposed shall be enabled, in fact, to the migrant displacement.

The important feature of the invention is that the presence of the cited plates, in essence, does not modify the form of the surface, since, practically, this surface results uniform and smooth.

Which implies an ingenious and simple solution to the outlined problems.

II—DRAWINGS

For greater clarity and comprehension of the object of the invention, it is illustrated with several figures, in which it has been represented schematically in some of its preferred forms; all this is done to serve as example, not limitative. Thus:

Figures 8, 9:
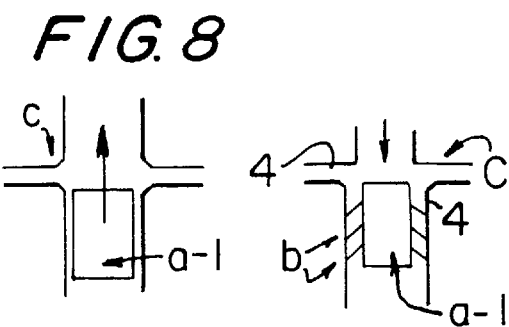

FIG. 8, it is a schematic view of the "stent", indicating how it can be easily slid through the interior of the vessel—until it is positioned—as long as this displacement is effected in the opposite direction to that of the bloodstream, since, in such case, the endowed external surface of the fastening plates behaves as if the surface were smooth and uniform, without opposing resistance.

FIG. 9, is other schematic view of the new "stent" or expander subject matter of the invention, to give a clear idea about the way in which its plates act against the internal surfaces of the artery, preventing their migration. In the figure, the arrow indicates the direction of the bloodstream and the corresponding direction of the plates with respect to such direction.

Figure 10:
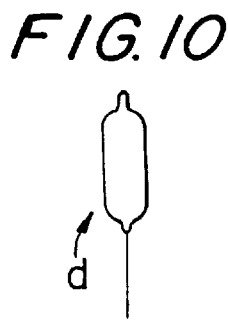
Figure 11:
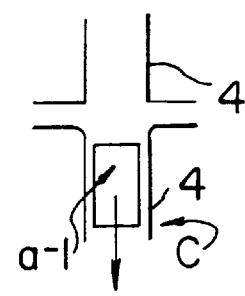

FIG. 10 illustrates schematically an inflatable balloon of the type used for the expansion of the "stent", when it is neither self-expandible, nor thermosensitive; and finally, FIG. 11 shows the possibility of migration of the "stent"—following the direction of the bloodstream that is indicated by the arrow—an instant before the means of positional anchorage, subject matter of the invention, is automatically enabled.

In the different figures, the same numbers of reference indicate corresponding or equal parts, and the sets of several elements have been indicated with letters.

LIST OF MAIN REFERENCES (a) expander (or "stent") in the form of wire mesh
(a') fretted expander
(a-1) generic expander
(b) means of unidirectional vascular anchorage of the expander
(a") balloon mounted expander
(c) vascular structure
(d) balloon expander
(1) tubular body of the expander (a)
(1') tubular body of the expander (a')
(2) anchorage piece that they compose (b)
(2') end of union of (2) with body (1)
(2") end of vascular anchorage (or free end).
(3) fret of (1')
(4) walls of application vessel
(40) fin (30) anchorage piece

III—MAIN OBJECT

For the specified effects, the endovascular expander, of a non migrant positioning; is of the type that includes a body (a) approximately tubular—generally structured by a wire mesh (1)—which, tensed in the sense of its diametrical expansion against the internal surfaces of the vessel (4) of application, it is able to be introduced in said vessel, in order to maintain or increase the lumen of the same; wherein outwardly the expander (a) possesses means (b) of unidirectional vascular anchorage in proximal arrangement to said tubular body (1) and in the sense of its generatrix; each one of such means (b) possesses two opposite ends of union (2') to the body (1) of the expander (a) and of vascular anchorage (20"), respectively—of which: that of union (20') is articulable with respect to said body (1), while that of vascular anchorage (20"), as of said link (20') is projected freely in proximal arrangement to the same body (1) of the expander (a); so that, being said expander (a) endovascularly applied—with the direction of the anchorage ends (20") in equal direction to that of the flow of the bloodstream—said means of anchorage (20") are capable of being open in contraposition to the migrant effect of the expander (a).

IV—DESCRIPTION

In general terms, (a) is the expander or "stent", that has as part of it, the means (b) of anti-migrant vascular anchorage.

Figure 1:
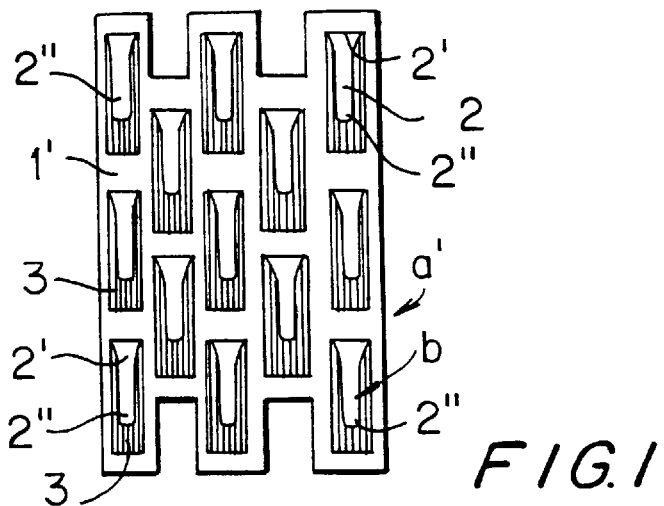
FIG. 1 is a schematic elevation of the expander formed by a pierced single piece. In its openings the projected means of vascular anchorage are shown; being in this case lengthened members that are born in an inflection point.
Figure 2:
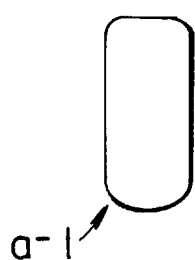
FIG. 2 is a schematic view of the body of an expander without the means of anchorage.
Figure 3:
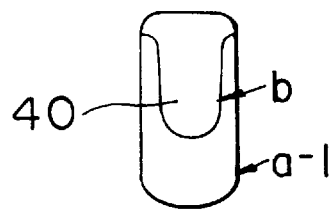
FIG. 3 is an elevational view of an expander with a means of anchorage lengthened in the form of a laminar fin, articulated in the zone where it begins with the body of the "stent".
Figure 4:
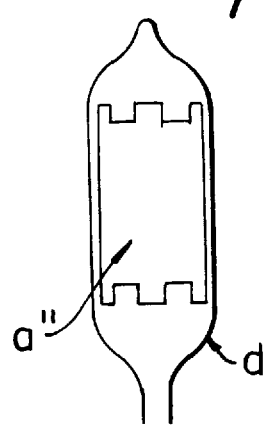
FIG. 4 is a schematic view of a "stent" expanded by means of an inflatable balloon.
Figure 5:
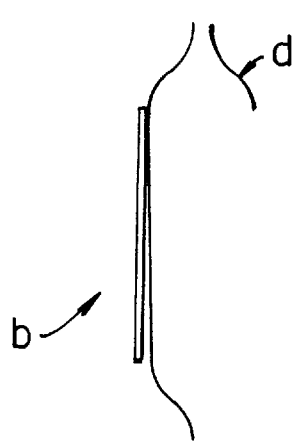
FIG. 5 is a schematic detail of the "stent" of FIG. 4, provided with a positional anchorage plate.
Figure 6:
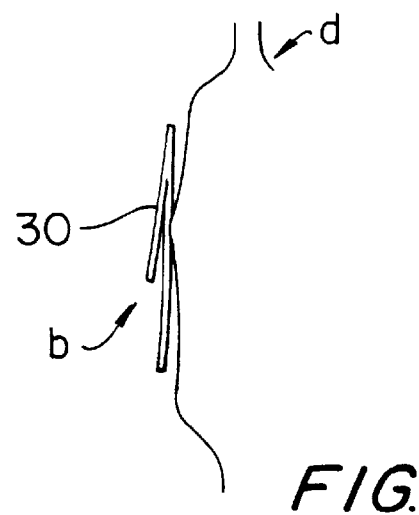
FIG. 6 is another detail of the "stent" endowed with plates in overlapped position or in a position arranged at regular steps.

The body of this "stent" (a) can be of wire, very thin, or a fretted expander (a') as shown in FIG. 1.

Figure 7:
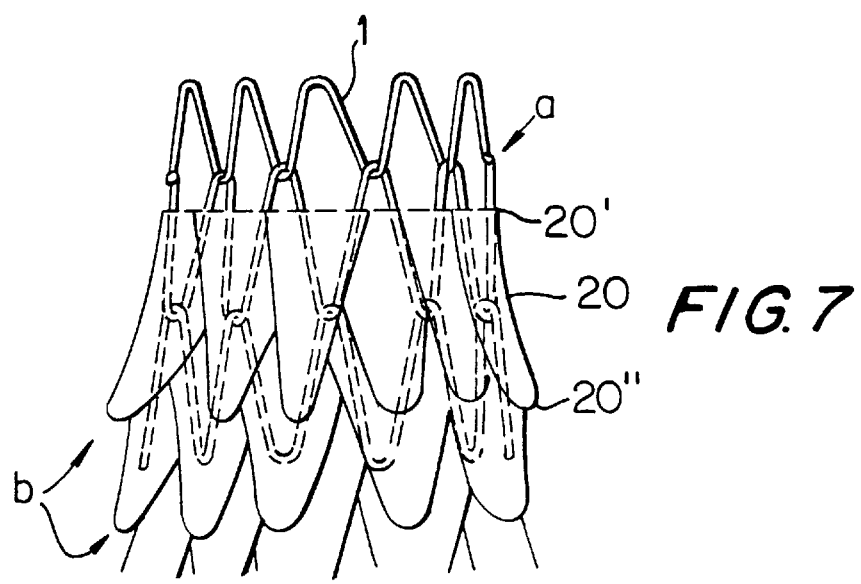
FIG. 7 is a schematic view of the "stent" very thinly structured in wire, and provided with the positional retention plates forming overlapped strings similar to fish scales.

In the first case, the tubular body (1) is a wire mesh (for example, of stainless steel), according to what is shown in FIG. 7; while in the case exemplified in FIG. 1, the expander (a') is a tubular body (1'), of very thin constitution, due to the fact of being affected of lengthened fret (3), as the fret (3) is shown in one embodiment in FIG. 1, of a plurality of parallel thin wires.

Also, this vascular expander—in its version (a) or (a')—may indistinctively be thermosensitive, self-expansible because of its own elastic report, or of expansion forced by the action of an inflatable balloon as well (b), FIGS. 4, 5, 6 and 10.

Now then; the new "stent",—endoluminally applicable to the vascular structure (c)—is characterized by the fact of possessing sideways articulable means (b) of unidirectional positional anchorage of the expander against the walls (4) of the vessel (c) of application; preventing thus its migration induced by bloodstream.

In the present document, it is said that the cited means of anchorage (b) act "in an unidirectional sense" due to their way of work, since, if the "stent" is with the ends free of such means (b), guided in the same direction of the bloodstream, the means of anchorage allows its easy sliding by the lumen of the vessel in opposed direction to such flow, so that it locates in the preset place (FIG. 8). While—once positioned by an introductory means or catheter conventional guide, and as soon as it tends to migrate dragged by the bloodstream (FIG. 11)—the expander (a-1), due to the generated friction, will display immediately its means (b), thus assuring thus its own anchorage in such position (FIG. 9).

Encompassing the constitution of such means of unidirectional vascular anchorage (b) of the "stent" (a), these can be laminar pieces, such as those shown in FIG. 7; or as those shown by the embodiment of the "stent" (a') of FIG. 1, indistinctively.

In any case, each piece (2) is preferably lengthened, provided with two opposite ends or end zones:

(A) an end (2') of union of the piece (20') with the body of the "stent". This end (2'), in the case of the example of embodiment of FIG. 7, forms in that zone a joint between the same piece (20) and the body (1) of the "stent" (a). While in the case of the example of the "stent" (a') formed by a single piece of expansible tubular body (1'), the cited anchorage pieces (2) have in their integral origin in the walls (1') of the "stent" (a') an inflection zone with it, and are projected in the fret (3) that affects said body (1');

(B) and a free end that is that of the vascular anchorage (2"), opposed to (2') and projected freely as end (2"), this forming an edge intended to be fastened against the walls (4) of the vessel, once the retention function of the pieces is enabled.

The cited pieces (20) that compose the means of positional anchorage (b) are sideways disposed on the body (1) of the "stent", in proximal position to said tubular body and in the sense of their generatrix. They can be mildly inclined as for their end (20') of articulation with the own body (1)—FIG. 7—, or contained in the fret (3) as of the inflection zone given by the same extremity (2"), FIG. 1.

In the (palmaz) "stent" expansible with balloon (d), of FIG. 1, its tubular body (1') operates as a cylinder with uniform expansion beginning at both ends. If the plates (2) are located in half of the fret (3) only held in the cephalic end (2'), these plates (2) will expand in a different form, having the free end (2") of said plates, the expansion tendency stronger, only limited by the resistance of the arterial wall (4), and the non elastomeric characteristics of the balloon (d), that will take a cylindrical shape (FIG. 1).

On the other hand, the cited pieces (2) can be formed by plates, wires and yet by pilose means components of a filiform structure.

In the preferred form of the embodiment that FIG. 7 illustrates, such pieces (20), as of their end of union and flexion (20'), are projected in the contour of the body of the "stent" forming different strings that overlap mutually as happens with the scales of a fish (according to what is explained in this regard in chapter I of this specification), being only seen the free ends or edges (20")that are, as it were said, precisely the ones intended to work against the internal surfaces of the vessel (4), if this were necessary.

In the case of being structured in wire, the referred pieces b) can be independently articulated, or each string around the body (1) can be formed by an only wire bent in "zigzag", its crests forming alternatively the union ends (20') and of vascular anchorage (20").

Furthermore, the configuration of the referred pieces (2) may be any of the appropriate ones, such as triangular [in which the free end of vascular anchorage (2") constitutes one of its vertex]; as well as oval, rectangular, trapecial or other polygonal; etc.

Essentially, this anchorage principle with the means (b) can be applied in any model of expander ("stent") or endoluminal prosthesis since, as it were said, its principal advantage is to provide a self-subjection mechanism against the wall of the vessel (4) to which it is applied.

When the "stent" or prosthesis is thoroughly displayed, in some instances one can be sure of its correct positioning using a ultrasonic endoluminal transducer.

The placement of the new "stent" can be made in the conventional form: puncturing the artery with a needle and introducing a guide cord with a caliber adequate and compatible to that of the artery to be treated. The needle is withdrawn and the advance is made with the introducer.

If it is necessary, previously the artery should be dilated by means of procrastinators with progressive calibers, before arriving to the adequate caliber.

Since this technique, obviously, is not a part of the object of the invention, is neither illustrated t nor described in greater details.

Once arrived to the adequate place, the cord and the procrastinator or baboon are withdrawn from its interior.

It is further relevant to be noticed that, in the case of the present embodiment, the surgeon must be cautious in introducing the "stent" in the opposite direction to the flow of the bloodstream (FIG. 8), and in such a way that the free ends (2') of the plates (2) result guided in the same direction of that flow (according to the arrow in FIG. 9), so that in case of existing an effect of migrant dragging (FIG. 11), the means of anchorage (d) will be automatically displayed (FIG. 9), keeping the "stent" stuck against the walls (4) of the vessel, in their correct position.

It is certain that, when the present invention is carried into practice, modifications regarding certain construction details and form may be introduced, without this being construed as geting aside of the fundamental principles, that are clearly expressed in the claim clauses that follow:

Having thus especially described and determined the nature of the present invention, and how can it be carried out, is it declared to claim, as to exclusive right and property:

1. An endovascular expander to be placed in a vessel carrying a bloodstream and to be retained in place, said endovascular expander comprising: a support forming said endovascular expander and a plurality of anchorage elements, wherein the anchorage elements are aligned in a plurality of rows which are overlapped one to each other, said plurality of anchorage elements having a general fish scale structure to prevent migration of the endovascular expander, wherein one end of each of said anchorage elements is connected to said support, and the other respective ends of said anchorage elements are free, whereby said anchorage elements open when pressured by blood flow and attach to the wall of the vessel thereby preventing the migration of the endovascular expander.

2. An endovascular expander, as claimed in claim 1, wherein said support is comprised of wire mesh.

3. An endovascular expander, as claimed in claim 1, wherein each of said anchorage elements is articulately connected to said support.

4. An endovascular expander, as claimed in claim 1, wherein the anchorage elements comprise plates.

5. An endovascular expander, as claimed in claim 1, wherein the anchorage elements comprise wires.

6. An endovascular expander, as claimed in claim 1, wherein the anchorage elements comprise a wire bent in zigzag, whose crests form alternately the ends connected to said support and the free ends.

7. An endovascular expander, as claimed in claim 1, wherein each of the anchorage elements has a filiform configuration.

8. An endovascular expander to be placed in a vessel carrying a bloodstream and to be retained in place, said endovascular expander comprising: a support forming said endovascular expander and a plurality of anchorage elements, wherein the anchorage elements are aligned in a plurality of rows which are overlapped one to each other, wherein one end of each of said anchorage elements is connected to said support, and the other respective ends of said anchorage elements are free, whereby said anchorage elements open when pressured by blood flow and attach to the wall of the vessel thereby preventing the migration of the endovascular expander.

* * * * *